(12) United States Patent
Shinohara et al.

(10) Patent No.: US 8,828,321 B2
(45) Date of Patent: Sep. 9, 2014

(54) REACTOR, MICRO-REACTOR CHIP, MICRO-REACTOR SYSTEM, AND METHOD FOR MANUFACTURING THE REACTOR

(75) Inventors: Yoko Shinohara, Chiba (JP); Minao Yamamoto, Chiba (JP); Masataka Shinogi, Chiba (JP); Haruki Kato, Chiba (JP)

(73) Assignee: Seiko Instruments Inc. (JP)

( * ) Notice: Subject to any disclaimer, the term of this patent is extended or adjusted under 35 U.S.C. 154(b) by 1759 days.

(21) Appl. No.: 11/338,293

(22) Filed: Jan. 24, 2006

(65) Prior Publication Data
US 2006/0169045 A1 Aug. 3, 2006

(30) Foreign Application Priority Data

Jan. 26, 2005 (JP) .................................. 2005-018352
Oct. 27, 2005 (JP) .................................. 2005-312290

(51) Int. Cl.
*G01N 27/00* (2006.01)
(52) U.S. Cl.
USPC ............................. 422/82.01; 422/50; 422/500
(58) Field of Classification Search
CPC ............................................. G01N 2291/0426
USPC .................. 422/102, 99, 68.1, 82.01
See application file for complete search history.

(56) References Cited

U.S. PATENT DOCUMENTS

| | | | | | |
|---|---|---|---|---|---|
| 4,735,906 | A | * | 4/1988 | Bastiaans | 436/527 |
| 5,413,955 | A | * | 5/1995 | Lee et al. | 438/456 |
| 6,653,091 | B1 | * | 11/2003 | Dunn et al. | 435/14 |
| 2003/0203271 | A1 | * | 10/2003 | Morse et al. | 429/38 |

FOREIGN PATENT DOCUMENTS

EP   1260267   11/2002

OTHER PUBLICATIONS

Patent Abstracts of Japan, publication No. 2003-240695, publication date Aug. 27, 2003.
Patent Abstracts of Japan, publication No. 2003-307480, publication date Oct. 31, 2003.
Patent Abstracts of Japan, publication No. 10-242795, publication date Sep. 11, 1998.
Patent Abstracts of Japan, publication No. 2003-114229, publication date Apr. 18, 2003.
Patent Abstracts of Japan, publication No. 03-094140, publication date Apr. 18, 1991.

* cited by examiner

*Primary Examiner* — Natalia Levkovich
(74) *Attorney, Agent, or Firm* — Adams & Wilks

(57) ABSTRACT

A reactor comprises a main body having a flow path substrate and a crystal substrate chemically bonded to the flow path substrate to form a flow path for running a sample to be measured and a reactor tank connected to the flow path. An adsorption film is disposed in the reactor tank for adsorbing a specific substance contained in the sample to be measured. A measuring device measures a physical quantity of the specific substance contained in the sample and adsorbed by the adsorption film.

15 Claims, 14 Drawing Sheets

REACTOR, MICRO-REACTOR CHIP, MICRO-REACTOR SYSTEM, AND METHOD FOR MANUFACTURING THE REACTOR

The present invention relates to a reactor utilizing a crystal oscillator and a method for manufacturing the same. In particular, the present invention relates to a reactor, a micro-reactor chip, and a micro-reactor system for the measurement of a viscosity, density and the like of a sample and the detection of the mass of a specific substance contained in a sample, as well as methods for manufacturing the same.

BACKGROUND OF THE INVENTION

1. Field of the Invention

The present invention relates to a reactor utilizing a crystal oscillator and a method for manufacturing the same. In particular, the present invention relates to a reactor, a micro reactor chip, and a micro reactor system for the measurement of the viscosity, density and the like of a sample and the detection of the mass of a specific substance contained in a sample as well as their manufacturing method.

2. Description of the Related Art

Active developments of small analysis systems called lab-on-a-chip have been under way in recent years. Small analysis systems of this type integrate element structures such as flow paths, reactor tanks, valves, sensors and the like on a small substrate to analyze gases and liquids flowing through these element structures. Examples of systems of this type can include biochips, which perform clinical inspection on the blood flowing through a minute flow path provided in a resin chip (Refer to Non-patent Reference 1, for example). Using such a small analysis system allows the fast analysis of a small quantity of a sample and therefore the reduction of burden on the side that provides the sample. Therefore, particularly the application of such a system to a living body is attracting attention.

Sensors utilizing various principles have been proposed for the sensor section, which is one of the components of the small analysis system. Above all, the use of QCM (Quarts Crystal Microbalance) and SAW (Surface Acoustic Waves) sensors is anticipated because these sensors are small-sized and capable of platy configuration and assumed to be easy to mount in systems.

QCM and SAW sensors utilize the oscillation of piezoelectric oscillators (particular crystal oscillators) and employ technologies for measuring the viscosity of samples that are in contact with the surface of the piezoelectric oscillator and minute mass adherent to the oscillator. More specifically, the QCM sensor oscillates at a specific frequency determined by the material properties and shape of the piezoelectric oscillator when an AC voltage is applied to electrodes formed on opposite surfaces of the piezoelectric oscillator. When a substance adheres to any electrode of the piezoelectric oscillator, the resonant frequency of the entire oscillator changes in response to mass adherent thereto. Also, the SAW sensor generates an elastic wave of a specific frequency determined by the frequency of the AC voltage, the shape of the electrode, the material properties of the piezoelectric element and the like when an AC voltage is applied to one of two pairs of blind-line electrodes thereof. The elastic wave generated is detected as a cyclic current by means of the other electrode pair due to the piezoelectric effects of the element. When a substance is then adhered between the two pairs of electrodes, the speed of the elastic wave changes in response to adherent mass. The phase, the frequency and the input/output impedance ratio also change between the voltage applied and the cyclic current detected. The technologies employed measure the mass of the substance adhered to the electrode by detecting the above-mentioned changes.

However, the detection of a specific substance is not possible with such mass measuring means. Therefore, a configuration is used which detects only a specific substance with means fixed in position for adsorbing or capturing the specific substance. As an example of such a configuration, a technique is known for using antigen-antibody reaction for protein detection (Refer to Patent Reference 1, for example. The utilization of such a configuration in a QCM or SAW sensor makes it possible to measure the minute mass of a specific substance to be measured. The utilization of the QCM or SAW sensor in the sensor section of a small analysis system therefore allows the high-precision measurement of a desired substance and the realization of an analysis system of a small-sized configuration.

The mounting of a crystal oscillator in an analysis system therefore requires a crystal oscillator to be mounted without any sample leaks. There are few disclosures and almost no specific disclosures concerning a method for mounting a crystal oscillator in a small analysis system. Consequently, such a method is analogized with typical methods for mounting a crystal oscillator as for use as a reactor. Conventional crystal oscillator mounting methods employed include methods for providing an O-ring at the interface between an analysis system base material and a crystal oscillator and pressing and contacting the oscillator and the system base material (refer to patent Reference 2, for example) and methods for bonding the base material and the oscillator (refer to Patent Reference 3, for example), and methods for gluing the base material and the oscillator.

[Patent Reference 1] JP-A-2000-338022
[Patent Reference 2] JP-A-11-14525
[Patent Reference 3] JP-T-2004-523150
[Non-Patent Reference 4] Proc. µTAS Symposium 2002, vol. 1, 187-189

However, methods that use an O-ring at the interface between the analysis system base material and the crystal oscillator require a mechanism for pressuring the crystal oscillator against the analysis system base material and have the problem that it is impossible to reduce the size of the analysis system itself. These methods also problematically require strict pressure adjustments because a small pressure on the crystal oscillator causes sample leaks between the system base material and the crystal oscillator while a large pressure on the crystal oscillator causes damage to the crystal oscillator.

Methods for gluing the analysis system base material and the crystal oscillator problematically require strict control of amounts of adhesive applied because the adhesive applied to the crystal oscillator or system base material reaches contaminates the inner walls of the flow path and reactor tank of the system and the sensing surfaces of sensors.

Methods for bonding the analysis system base material and the crystal oscillator require heat treatments at high temperatures and produce residual stresses in the crystal oscillator because of the different coefficients of thermal expansion of the crystal oscillator and the system base material after bonding. Consequently, these bonding methods problematically suffer from a drop in sensitivity of the crystal oscillator due to failure to operate at a desired frequency.

In any of the gluing and bonding methods, the fixed region of the crystal oscillator relative to the system base material is increased and the region fixed to the system base material acts as a fixed end. Oscillations reflected from the fixed region cause the crystal oscillator to oscillate in an unintended oscillation mode (spurious). Desired oscillations cannot be separated from spurious oscillations and there is also a problem of a drop in sensor sensitivity. When, on the other hand, the fixed region is reduced, a sufficient fixing strength cannot be obtained relative to the internal pressure generated from the supply of the reagent and there is also a problem of liquid leaks from the boundary between the system base material and the crystal oscillator.

SUMMARY OF THE INVENTION

To attain the above-mentioned problems, the present invention is characterized by a configuration described below. That is, in a reactor having a flow path for running a sample to be measured, a reactor tank connected to the flow path and having capture means for capturing a specific substance contained in the sample to be measured, and a liquid-phase sensor for measuring a physical quantity of the specific substance contained in the sample to be measured which has been caught by the capture means, the reactor tank includes a substrate formed with a concave portion and made of a material that chemically bonds to silicon contained and a crystal substrate disposed to cover the concave portion and bonding to the substrate through a chemical bond. The liquid-phase sensor includes the crystal substrate, a crystal oscillator disposed on a surface of said crystal substrate and having electrodes formed with said capture means and frequency measuring means connected to said electrodes for measuring a change in frequency of said crystal oscillator.

In addition, a micro reactor chip according to the invention comprises the reactor and includes a liquid introduction port formed on the substrate for introducing the sample to be measured to the reactor tank through the flow path and a liquid discharge port formed on the substrate for discharging the sample to be measured from the reactor tank through the flow path.

The micro reactor system according to the invention includes the micro reactor chip, pump means connected to the liquid introduction port or the liquid discharge port for feeding the sample to be measured, liquid feed control means for controlling the opening and closing of the valve mechanism and control means for controlling the pump means, the frequency measuring means, and the liquid feed control means.

In addition, a micro reactor chip manufacturing method according to the invention includes a first step of forming a concave portion in a substrate, a second step of forming an electrode on a crystal substrate, and a third step of causing the substrate and the crystal substrate to bond to each other through a chemical bond to form a reactor tank by laying the substrate and the crystal substrate over the concave portion.

According to a reactor, micro reactor chip, and micro reactor system and their manufacturing methods of the invention, the configurations and the manufacturing methods are simple but ensure that the sensor, chip base material, and crystal oscillator can be integratedly formed. the configurations and the manufacturing methods also realize high-sensitivity detection because of the absence of residual stresses on the crystal oscillator and unwanted oscillation modes.

DETAILED DESCRIPTION OF THE PREFERRED EMBODIMENTS

The present invention will be described in detail with reference to the drawings. Note that the invention is not limited to the embodiments described below.

Figure 1A:
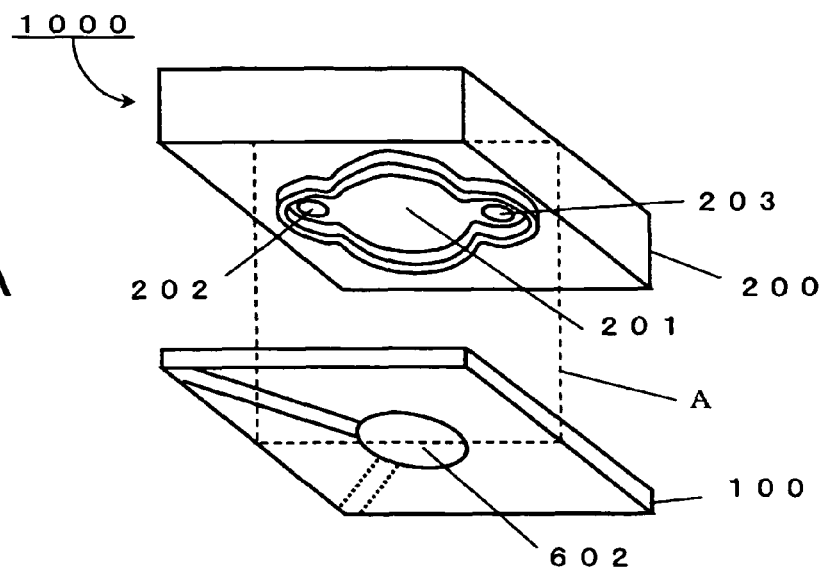
FIG. 1A-1C are an explanatory view of the configuration of a reactor according to one embodiment of the present invention.
Figure 1B:
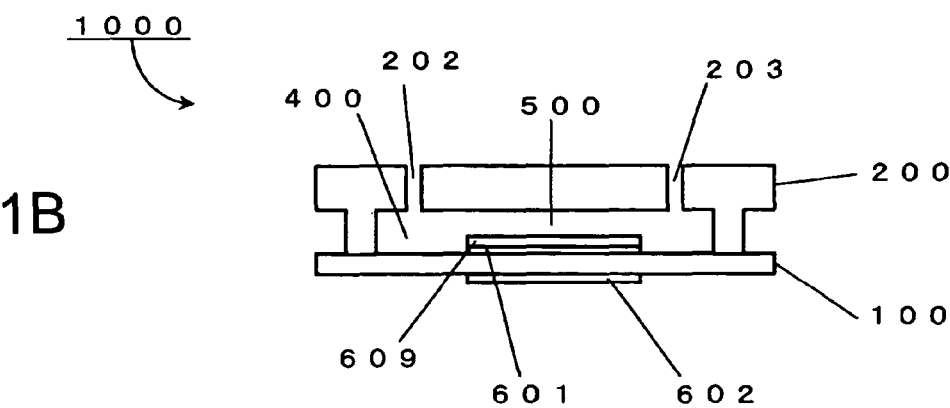
Figure 1C:
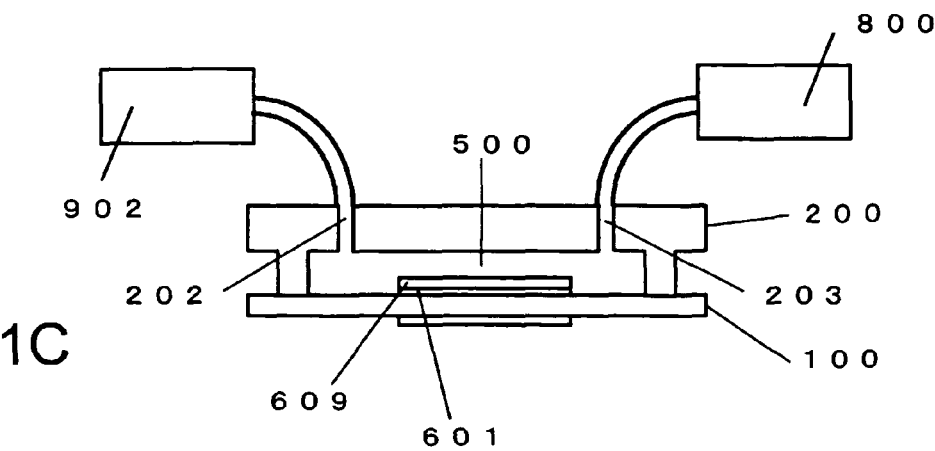

FIG. 1 is a diagram describing the configuration of a reactor 1000 according to the invention. FIG. 1A is an exploded view showing the partial configuration of the reaction 1000 FIG. 1B is a cross sectional view of the reactor 1000 (the cross section of surface A in FIG. 1A). FIG. 1C is an explanatory view showing a configuration for feeding a reagent into the reactor 1000. The reactor 1000 is designed to analyze the interaction of biomolecules such as protein, specifically, to bond analyte to a ligand and detect the state of the resulting bond reaction (such as bond strength, bond speed, and dissociation constant, for example).

First Embodiment

The reactor 1000 includes a main body having a crystal substrate 100 and a flow path substrate 200 bonded together. The crystal substrate 100 has a generally flat shape with opposed major surfaces and will be described first. A detection electrode 601 and an opposite electrode 602 are provided on both surfaces of the crystal substrate 100. In addition, an adsorption film 60 for adsorbing only a specific substance is provided on a surface of the detection electrode 601. The flow path substrate 200 is provided with a groove 201 as well as a liquid an introduction port 202 and a liquid discharge port 203, which are through-holes provided in the groove 201. A portion of the groove 201 is widened.

The crystal substrate 100 and the flow path substrate 200 are integrated to form the reactor 1000. Specifically, one surface of the crystal substrate 100 provided with the detection electrode 601 is bonded to and integrated with one surface of the flow path substrate 200 provided with the groove, thereby forming a flow path 400 between the groove 201 and the surface of the crystal substrate 100. In addition, the widened region of the groove 201 is then formed into a reactor tank 500 and the detection electrode 601 will be provided in the reactor tank 500.

When a sample liquid fed is to the liquid introduction port 202 by means of a pump 902 connected to the liquid introduction port 202, the sample liquid can be made to flow through the flow path 400 and the reactor tank 500 and via the liquid discharge port 203 to a waste liquid tank 800. The detection electrode 601 for measuring a specific substance contained in the sample liquid and the surface of the adsorption film 609 will therefore be soaked with the sample liquid.

A description will then be made of a technique for measuring the mass of a substance adhered to the detection electrode 601 through an electrical system connected to the detection electrode 601 and the opposite electrode 602 provided on the crystal substrate 100 and electric signals. the reactor 1000 described here uses a AT-cut crystal plate. The AT-cut crystal plate will generate thickness shear vibrations when a cyclic electric potential difference is provided across the thickness thereof.

Figure 2A:
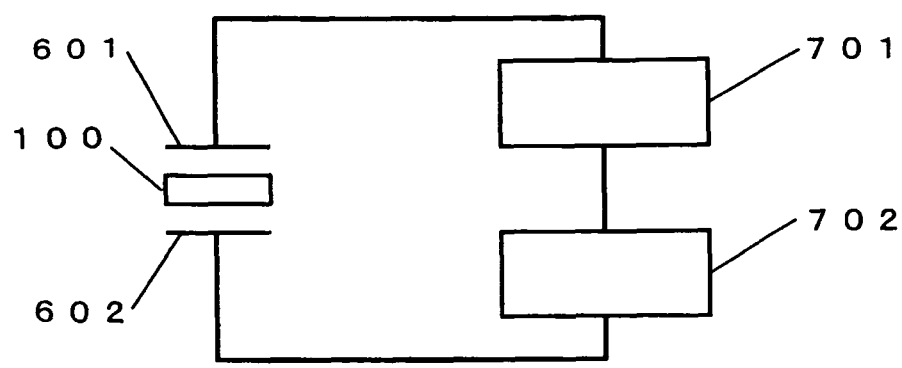
FIG. 2A-2B are a circuit diagram of a sensor section according to one embodiment of the present invention.
Figure 2B:
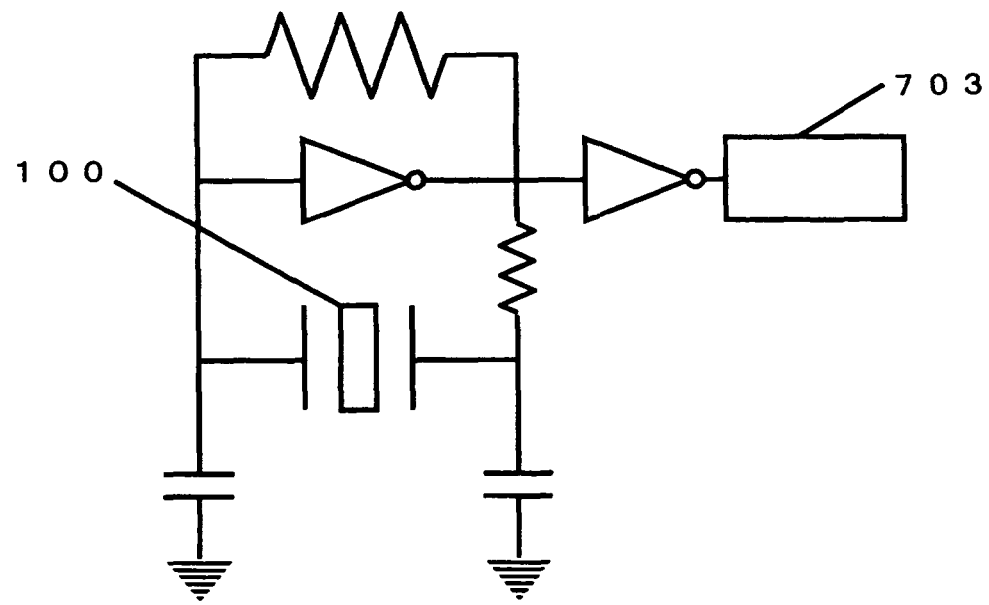

FIG. 2A shows an electrical configuration where a crystal substrate 100 is connected to a detection electrode 601 and an opposite electrode 602. A variable-frequency AC power supply 701 and an ammeter 702 are connected in series to each other. One end is connected to the detection electrode 601 and the other end to the opposite electrode 602. The application of an AC voltage to the detection electrode 601 and the opposite electrode 602 from the AC power supply 701 causes a current flowing through the ammeter 702 to change in response to the frequency of the voltage applied. The frequency of the voltage applied where the current reaches a maximum value is resonant frequency. When a substance to be measured adheres to the detection electrode 601, the resonant frequency drops in response to the mass of the adherent substance. Therefore, the mass of the substance adherent to the detection electrode 601 can be measured by detecting a change in resonant frequency. As shown in FIG. 2B, the mass of the substance adherent to the detection electrode 601 can also be similarly measured by the Kollwitz oscillation circuit to cause the crystal oscillator to oscillate and then measuring a change in resonant frequency using a frequency counter 703.

Figure 3A:
FIG. 3A-3G are a diagram showing a process for manufacturing the reactor according to one embodiment of the present invention.
Figure 3B:
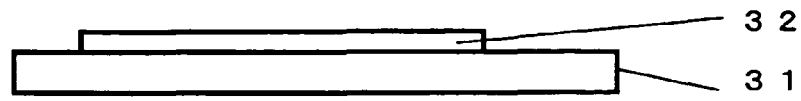
Figure 3C:
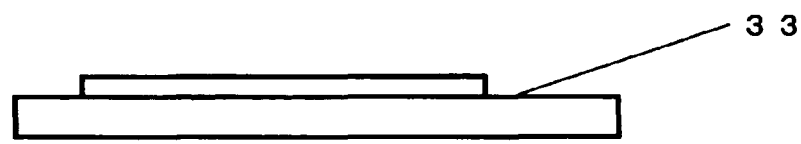
Figure 3D:
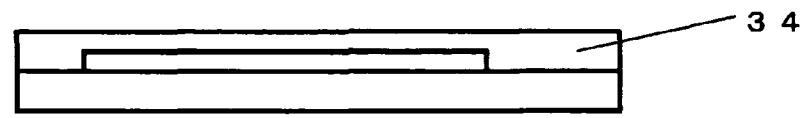
Figure 3E:
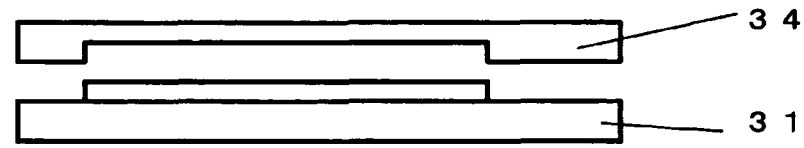
Figure 3F:
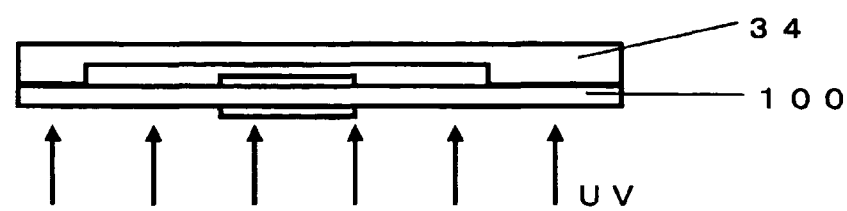
Figure 3G:
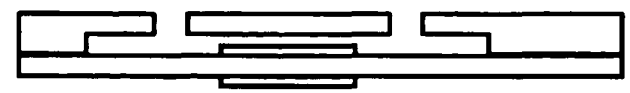

A method for manufacturing a reactor 1000 according to the invention will then be described below. A thin film of chrome or titanium is first formed on an electrode-forming region on both surfaces of a AT-cut crystal plate 100 which is then deposited or sputtered with gold to prepare a detection electrode 601, an opposite electrode 602 and wiring to both electrodes. As shown in FIG. 3, a resist 32 (FIG. 3B) is then formed on a cleaned silicon wafer 31 (FIG. 3A), which is then coated with Teflon 33 (FIG. 3C). Polydimethylsiloxane (PDMS) 34 is then poured onto the silicon wafer and allowed to cure (FIG. 3D). The PDMS 34 is then peeled from the silicon wafer 31 (FIG. 3E). This forms a groove in the PDMS 34. The PDMS 34 is then laid on the crystal plate 100. When the crystal substrate 100 side is then irradiated with ultraviolet light (light source: UV excimer lamp; wavelength: 172 nm), the silicon-carbon bond between the crystal and the PDMS is cut, thus causing the crystal and the PDMS to bond to each other by means of a siloxane bond (which bonds silicon and oxygen to each other) (FIG. 3F). The liquid introduction port and the liquid discharge port are then cut to form the reactor 1000 (FIG. 3G).

Because the crystal and the PDMS are bonded to each other by means of covalent bond, the crystal and the PDMS plate can be bonded to each other with a high strength. Because only ultraviolet light is used for irradiation in the covalent bond, none of these members are heated and no residual stresses are generated in the crystal after bonding. Because of its low rigidity, the PDMS plate 34 also never attenuates the oscillation of the crystal even when bonded to the crystal. In the configuration according to the invention, the flow path substrate is provided with an elongate bank structure and the upper of the bank structure is bonded to the crystal substrate 100 to hold a crystal oscillator. Because the crystal oscillator is held with a low-rigidity structure as described above, the low-rigidity structure never attenuates the oscillation of the crystal. The resonant frequency of the crystal oscillator can therefore be captured accurately, which allows the mass of a substance on the crystal oscillator to be measured with high sensitivity.

In the manufacturing method described above, ultraviolet light is used for irradiation when the crystal substrate 100 and the PDMS 34 are bonded to each other. If the bonding surfaces are clean enough, both of the members can be bonded to each other by simply pressing these members to bring one member into contact with the other. However, the two members, when positioned, can be bonded to each other in a position, not in a predetermined positional relationship. After ethanol is applied to one bonding surface, one member is therefore aligned with the other, when the crystal substrate 100 and the PDMS 34 are not bonded to each other because of the ethanol layer on the bonding surface. When the two members can be aligned with each other and are pressed to bring one member into contact with the other, the ethanol is carried away, thus allowing the planned bonding surfaces to be bonded to each other under pressure.

While the crystal substrate 100 and the PDMS plate 34 are bonded to each other by means of covalent bond, the electrode (gold) on the crystal substrate 100 cannot bond to and simply self-sticks to the PDMS plate 34. Even if the electrode is not bonded to the crystal substrate 100, however, there is no fear that the electrode section in the bonding region will have liquid leaks and the like because the electrode section has a width of a few hundred nm or so.

In addition, reactive ion etching (RIE) by oxygen is performed on the planned boding surfaces of the crystal substrate 100 and the PDMS plate 34 to activate the planned boding surfaces. After that, the crystal substrate and the PDMS plate can also be bonded to each other by laying the PDMS plate 34 on the crystal substrate 100 and using ultraviolet light for irradiation. The crystal substrate and the PDMS plate can also be bonded to each other by applying silicone oil to the crystal substrate 100, laying the PDMS plate 34 on the crystal substrate 100, and using ultraviolet light for irradiation. Using these methods allows a high bonding strength to be maintained even if there are contamination on and minute irregularities in the planning surfaces of the crystal substrate 100 and the PDMS plate 34.

In addition, the formation of the flow path substrate uses a method for pouring liquid silicone resin onto the surface of a mold to transcribe mold irregularities, thus allowing the flow path substrate to be manufactured easily. Because the mold with a resist formed on a silicon wafer can be used many times, it is easy to mass produce the flow path substrate.

An example of the reactor manufacturing process has been described above. However, it is also possible to use, as a system base material, other types of silicon resin and silicon-free resin with the surface thereof coated or sputtered with silicon dioxide.

A method for forming an adsorption film to be provided on a detection electrode 601 will be described below. A method for preparing an adsorption film 609 with a self-assembled monolayer (hereinafter referred to as SAM) will be described below as an example of the method. Pure water is first poured into the flow path 400 for cleaning purposes. A SAM reagent (carboxyl-terminated disulfide type) is then poured on the detection electrode 601 to form the SAM thereon, which is then cleaned with phosphoric acid buffer. Hydroxysuccinic acid imide is then poured onto the SAM to activate the SAM, which is cleaned with phosphoric acid buffer again. An immobilization antibody is then mixed with the phosphoric acid buffer and the resultant mixture is poured onto the SAM to immobilize the antibody on the SAM. A method for forming the adsorption film 609 after the gluing and bonding of two substrates has been described above. However, it is also possible to form an adsorption film 609 during formation of the crystal wafer and then glue or bond the two substrates to each other.

A process for detecting a specific substance in a sample flowing through a reactor 1000 will be described below. The detection of a biopolymer, particularly a protein, will be described below as an example of a specific substance.

A sample liquid is poured into the liquid introduction port 202 of the reactor 1000. The sample liquid flows through the flow path 400 and to the reactor tank 500. The reactor tank 500 is filled with the sample liquid and an adsorption film 609 provided on the surface of a detection electrode 601 is soaked with the sample liquid, at which time an antibody in the adsorption film 609 captures and fixes a specific antigen contained in the sample liquid. An resultant increase in mass of the antigen on the detection electrode 601 causes a change in the resonant frequency on the detection electrode 601 side. An ammeter 702 can measure the change to measure the mass of the substance fixed to the adsorption film 609. Before the change in the resonant frequency can be measured, the frequency of an applied signal from a power supply 701 is first changed gradually with no mass on the detection electrode 601, under which condition, the resonant frequency is then measured.

The frequency of the applied signal is then limited to a frequency close to the resonant frequency to repeat a gradual change in the frequency of the applied signal. Each time the gradual change is repeated, the ammeter 702 is used to determine the frequency at which the current reaches a maximum value. With the applied signal from the power supply 701 as a white noise, it is also possible to break a current value measured on the ammeter 702 into frequency components using FFT and determine a change in the resonant frequency. With a clear relation between the frequency of the applied signal and the current value from the ammeter, it would also be possible to estimate the resonant frequency through a curve fit and the like after the measurement of the frequency of the applied voltage and the current value at several points.

The configurations and manufacturing method described above, though simple, makes it possible to maintain a high sensitivity without residual stresses on the crystal oscillator and unwanted oscillation modes and to ensure that the system base material and the crystal oscillator can be integrated with each other.

Second Embodiment

Figure 4:
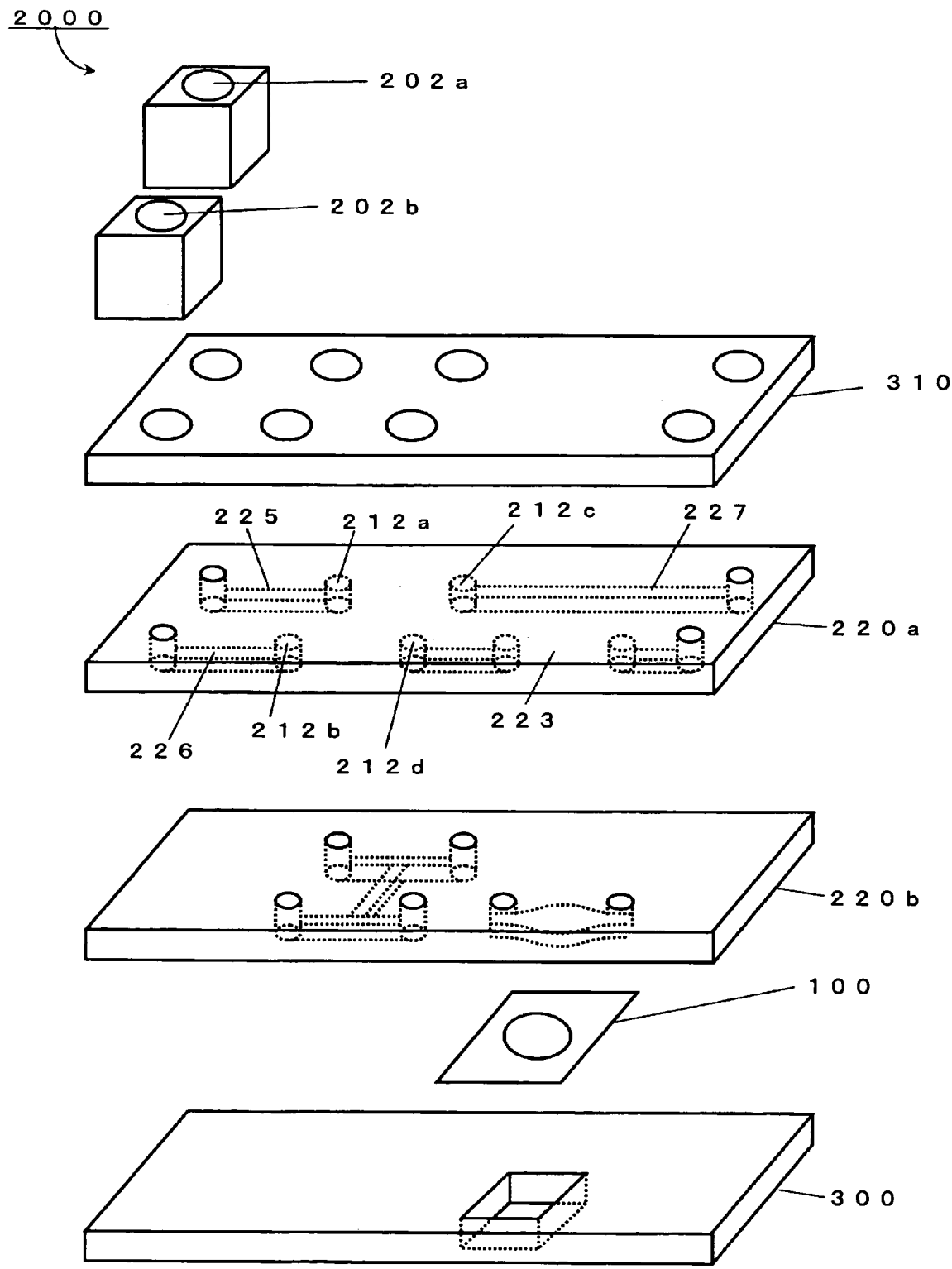
FIG. 4 is a perspective view of a micro reactor chip according to one embodiment of the present invention.
Figure 5A:
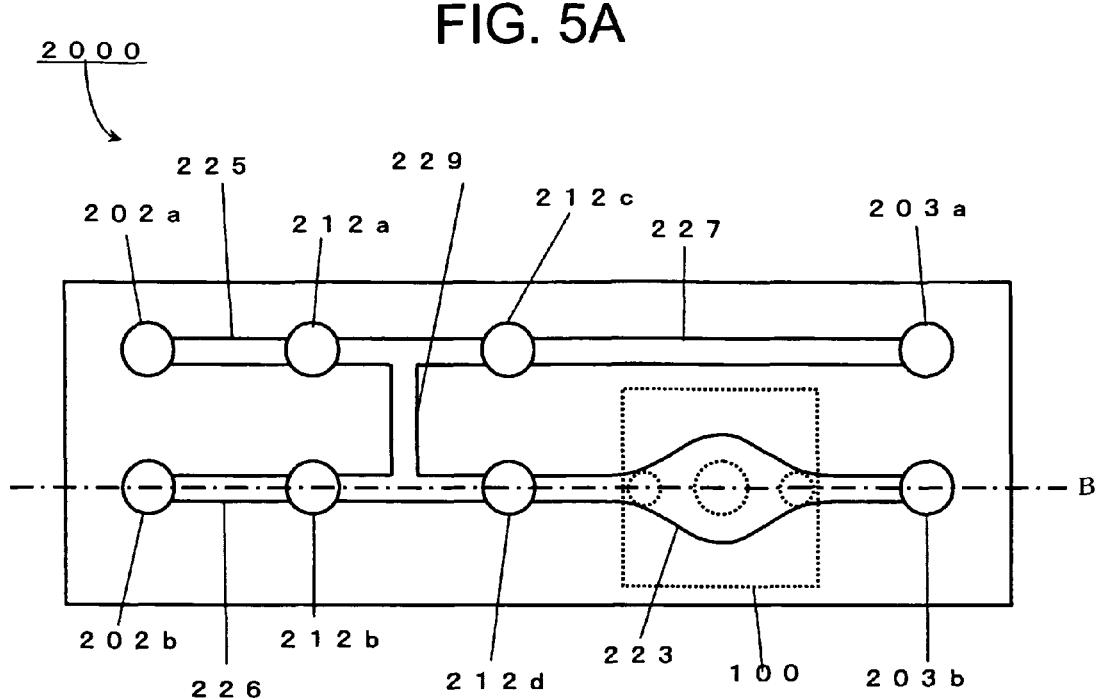
FIG. 5A-5B are a plan view of the micro reactor chip according to one embodiment of the present invention.
Figure 5B:
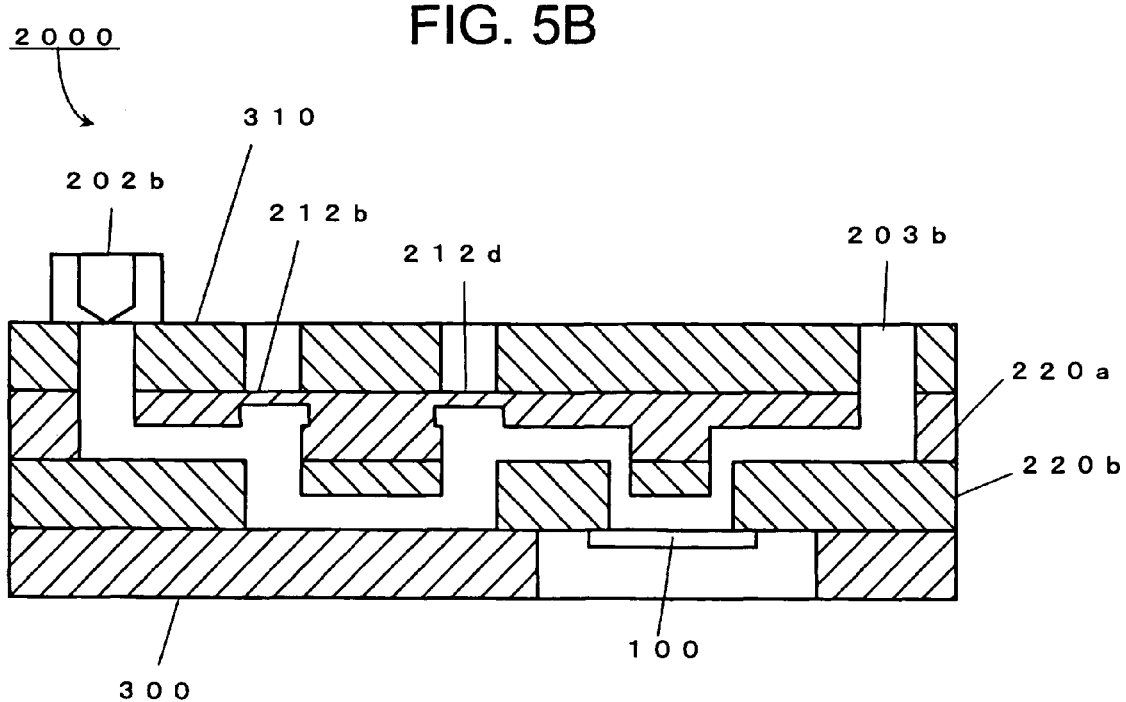

FIG. 4 is an exploded perspective view of a micro-reactor chip (hereinafter "micro reactor chip") 2000 according to the invention. FIG. 5A and FIG. 5B show a schematic plan view of the micro reactor chip and a cross sectional view of the micro reactor chip (the cross section taken along the surface B in FIG. 5A), respectively. The same descriptions as in the first embodiment will not be made below.

The micro reactor chip 2000 includes a generally flat crystal substrate 100 having opposed major surfaces, flow path substrates 220a and 220b, and a holding substrate 310, all of which are laminated together. Each of the members will be described below. The crystal substrate 100 is configured in the same way as in the first embodiment. The flow path substrates 220a and 220b are formed with a minute concave portion and a through-hole while the holding substrate 310 and the substrate 300 are formed with a through-hole. These members are laminated together and integrated with one another, thereby providing a reactor tank 223, where reaction occurs, a sample liquid supply path 225 for feeding a sample liquid for analysis, a buffer liquid supply path 226 for feeding a buffer liquid having a flow path cleaning function and a buffer function (dissociation function), and a waste liquid path 227 leading to a liquid discharge port 203a. Specifically, the buffer liquid supply path 226 and the reactor tank section 223 are connected to each other, thereby forming a first flow path. The sample liquid supply path 225 and the waste liquid path 227 are connected to each other, thereby forming a second flow path. In addition, a branch flow path section 229 connected to the upstream side away from the reactor tank section 223 of the first flow path is provided starting on the second flow path. The crystal substrate 100 and the flow path substrates 220b to form the reactor tank section 223, which is almost the same way as in the first embodiment described earlier. Moreover, the flow path substrates 220b is then integrated with the reactor tank section 223, thereby forming a flow path. The flow path and the reactor tank section 223 will then be connected to each other.

A port 202a for sample liquid introduction, shaped like a cup to which drops of a sample liquid is fed, is provided at an end of the sample liquid supply path 225 (the end on the opposite side of the waste liquid path 227). Similarly, a port 202b for buffer liquid introduction, shaped like a cup to which drops of a buffer liquid is fed, is provided at an end of the buffer liquid supply path 226 (the end on the opposite side of the reactor tank section 223). While the waste liquid path 227 is connected to a liquid discharge port 203a, the reactor tank section 223 is connected to a liquid discharge port 203b.

The second flow path including the sample liquid supply path 225 and the waste liquid path 227 is provided with a valve 212a and a valve 212c on the upstream side of the branch flow path section 229 and on the downstream side of the branch flow path section 229, respectively. The first flow path including the buffer liquid supply path 226 and the reactor tank section 223 is also provided with a valve 212b and a valve 212d on the upstream side of a portion connected to the branch flow path section 229 and on the downstream side of a portion connected to the branch flow path section 229, respectively.

Figure 8:
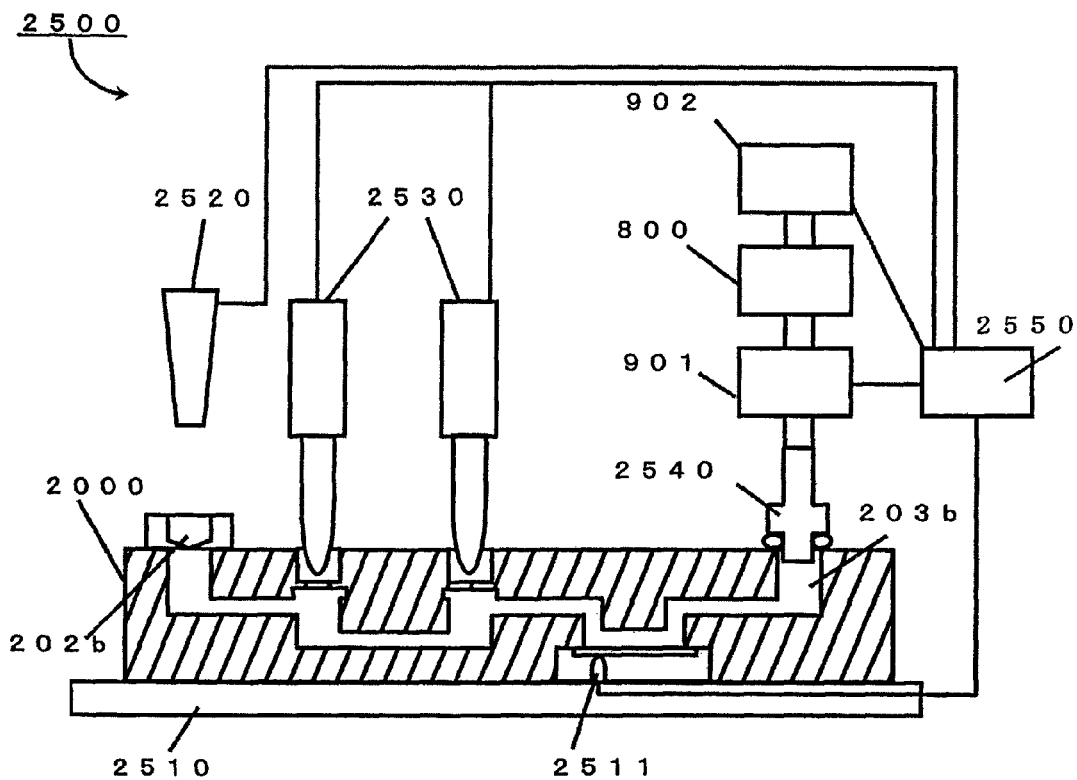
FIG. 8 is a cross sectional view showing a micro reactor system according to one embodiment of the present invention.

The configuration of a micro-reactor system (hereinafter "micro reactor system") 2500 using a micro reactor chip 2000 will be then described below with reference to a configuration diagram in FIG. 8. The micro reaction chip 200 is first provided on a stage 2510. A contact pin 2511 is fixed to the state 2510. When the micro reactor chip 2000 is provided, the contact pin 2511 is brought into contact with wiring from a detection electrode 601 of a crystal substrate 100 and an opposite electrode 602 under a constant pressure, thereby providing electrical conduction.

A drop port 2520 for feeding drops of a sample liquid and a buffer liquid is also disposed directly above each of the port 202a for sample liquid introduction and the port 202b for buffer liquid introduction of the micro reactor chip 2000 provided on the stage 2510. A linear actuator 2530 for valve opening and closing is disposed directly above the valve 212. A suction port 2540 is connected to each of liquid discharge ports 203a and 203b. The suction port 2540 on the liquid discharge port 203a side is connected to a waste liquid tank 800 while the suction port 2540 on the liquid discharge port 203b side is connected through a trace liquid feed pump 901 to the waste liquid tank 800. In addition, a pump 902 is connected to the waste liquid tank 800. The trace liquid feed pump 901' and the pump 902 can suction a fluid from the waste liquid path 227 and the reactor tank section 223.

Moreover, a control circuit 2550 is connected to each of the contact pin 2511, drop port 2520, linear actuator 2530, trace liquid feed pump 901, and pump 902.

Figure 9A:
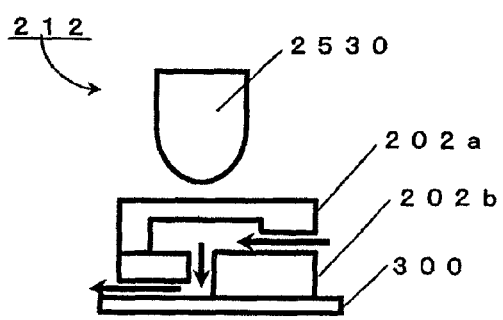
FIG. 9A-9B are a cross sectional view showing the operation of a valve of the micro reactor chip according to the invention.
Figure 9B:
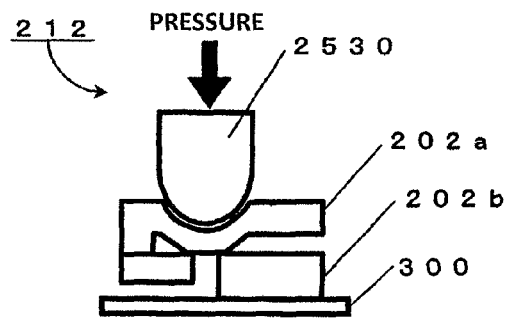

Liquid feeding for the micro reactor system 2500 will be described below. A drop port 2520 is disposed directly above a port 202a for sample liquid introduction and a port 202b for buffer liquid introduction. This causes a constant amount of a sample liquid or buffer liquid to drop and be fed to a chip without any contact. The liquid flowing through a valve 212 is fed under the control of the valve 212. The valve is opened and closed by a linear actuator 2530 disposed directly above the valve. The valve 212 has an elastic deformation portion. When pressed by the linear actuator 2530, the elastic deformation portion shuts off the flow path (FIG. 9B). The elastic deformation portion deforms elastically and ceases to deform if a pressure is relieved, thereby opening the flow pass (Refer to FIG. 9A).

Consequently, the valve can be open and closed by simply providing a force to the valve from outside the chip. A liquid is discharged from the chip through liquid discharge ports 203. A suction port 2540 is connected to each of the liquid discharge ports 203. Because an O-ring is fit in a stepped portion in an outside surface, the O-ring becomes deformed when the suction port 2540 is brought into contact with the liquid discharge port 203 under pressure. The trace liquid feed pump 901 and the pump 902 can therefore communicate with the chip without any negative-pressure loss, thus allowing an accurate liquid feed. The liquid from the chip flows through the suction port 2540, being ultimately accumulated in a waste liquid tank 800. A control circuit is responsible for all of the liquid feed described above and detection by sensor operation at a predetermined timing.

With the configuration as described above, the micro reactor system 2500 can be connected to the micro reactor chip 2000 through only contact under pressure without utilizing screws. This allows the system to be easily connected to and disconnect from the chip. The configuration described above is an example of the configuration of the system. The connection between the chip and the system is not limited to the above configuration.

A method for manufacturing a micro reactor chip 2000 will be then described below. As with the first embodiment, a crystal substrate 100 is formed by forming an electrode on a polished AT-cut crystal plate 100. As with the first embodiment, flow path substrates 220a and 220b are formed with a minute concave portion by using polydimethylsiloxane (PDMS) and photolithography. After the application of a silica solution to the surface of an acrylic plate, a holding substrate 310 is heated, thereby forming thin glass the surface thereof. A substrate 300 is a glass plate.

In the bonding process, silicon oil is first to the planned bonding surfaces of a flow path substrates 220b and a crystal substrate 100. One member is then brought into contact with the other. The crystal substrate 100 side is then irradiated with ultraviolet light to bond flow path substrates 220b and a crystal substrate 100 to each other. The flow path substrates 220a and 220b are then brought into contact with the crystal substrate 100 for bonding purposes. The planned bonding surfaces of the flow path substrates 220b and a substrate 300 are then irradiated with oxygen plasma and the flow path substrates 220b and a substrate 300 are brought into contact with each other for bonding purposes. Finally, the planned bonding surfaces of a holding substrate 310 and the flow path substrates 220a are irradiated with oxygen plasma and the holding substrate 310 and the flow path substrates 220a are brought into contact with each other for bonding purposes.

A port 202b for buffer liquid introduction and a port 202b for buffer liquid introduction, both fabricated of polycarbonate resin, are connected to a plate-like chip that includes these four members laminated together, thereby providing a complete micro reactor chip 2000. Note that other resin materials or more desirably any material with good heat resistance can be substituted for acrylic and polycarbonate mentioned as member materials.

Figure 6:
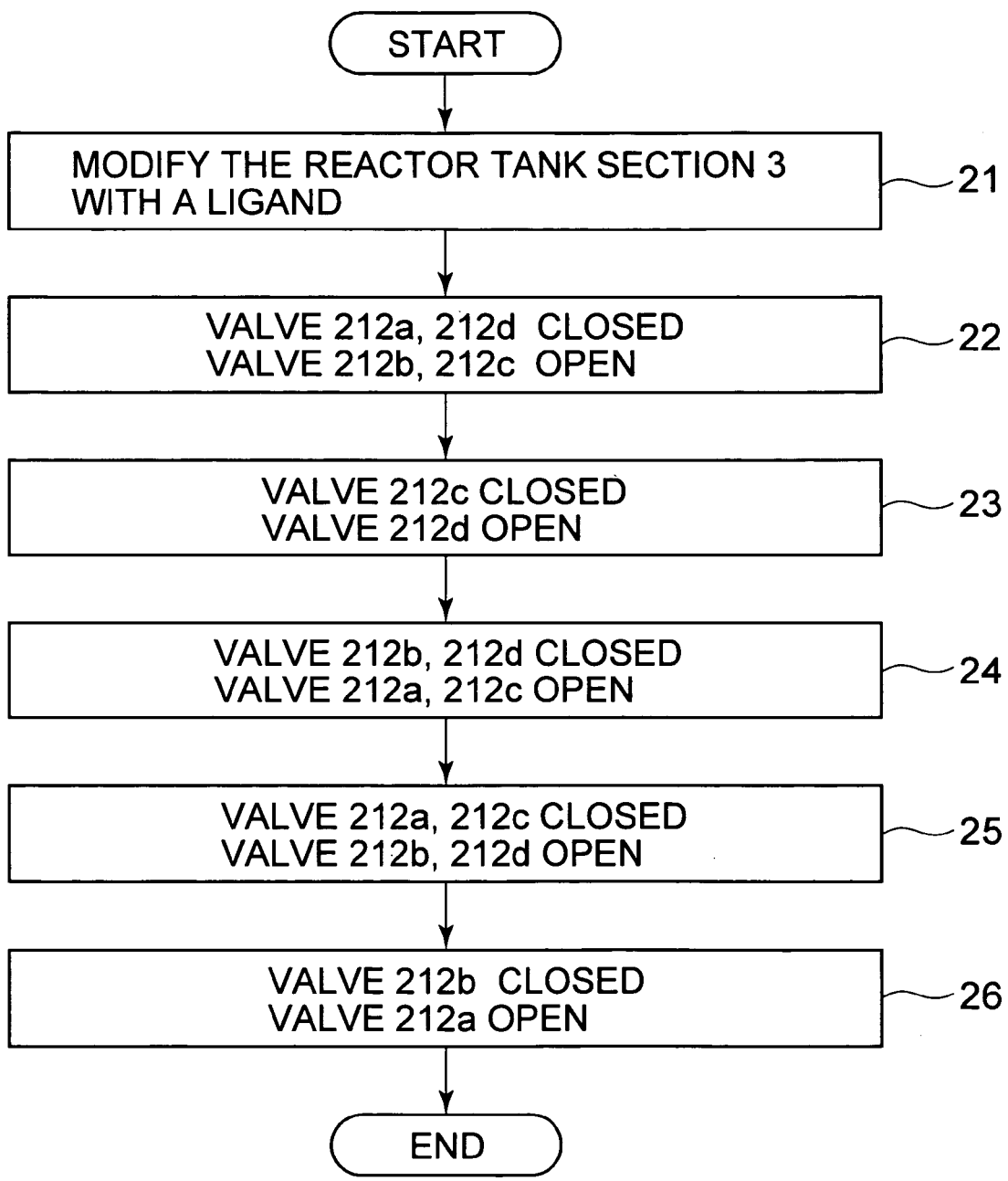
FIG. 6 is a flow chart showing the detection operation of the micro reactor chip according to one embodiment of the present invention.

An analysis method according to the invention using the micro reactor system 2500 will be described specifically with reference to a flow chart in FIG. 6.

Figure 7A:
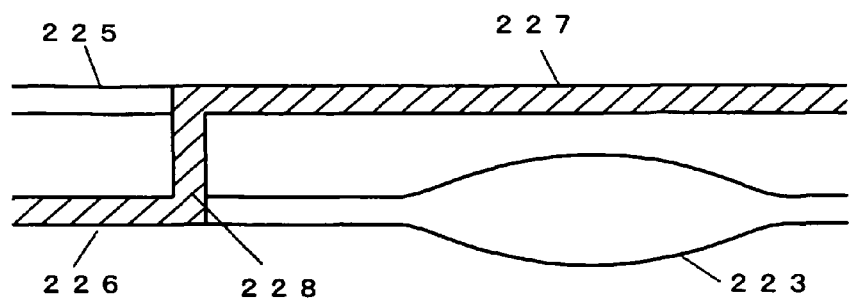
FIG. 7A-7D are a cross sectional view showing the liquid feed state for the micro reactor chip according to one embodiment of the present invention.

A reactor tank section 223 is first modified with a ligand (Step 21). Specifically, an adsorption film 609 is formed through a detection electrode 601 provided in a crystal substrate 100 in the reactor tank section 223. Air relief is then done to discharge air from each flow path. A buffer liquid is then dropped a port 202b for buffer liquid introduction and a sample liquid is dropped into a port 202a for sample liquid introduction. Valves 212a and 212d are first closed and valves 212b and 212c are opened before a pump 902 is operated. This causes the buffer liquid dropped into the port 202b for buffer liquid introduction to be suctioned and fed through a buffer liquid supply path 226, a branch flow path section 229, and a waste liquid path 227 to a waste liquid tank 800. Air is then relieved of the buffer liquid supply path 226, the branch flow path section 229, and the waste liquid path 227 (Step 22) to fill these components with the buffer liquid as shown in FIG. 7A. The valve 212c is then closed and the valve 212d is opened to guide the buffer liquid in the buffer liquid supply path 226 to the reactor tank section 223 and to cause the buffer liquid to be suctioned and fed to the waste liquid tank 800.

Figure 7B:
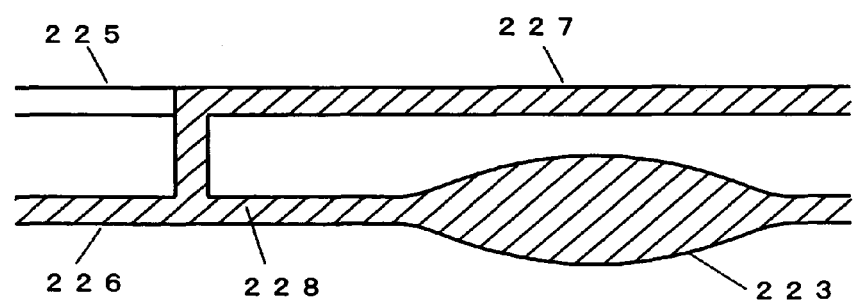
Figure 7C:
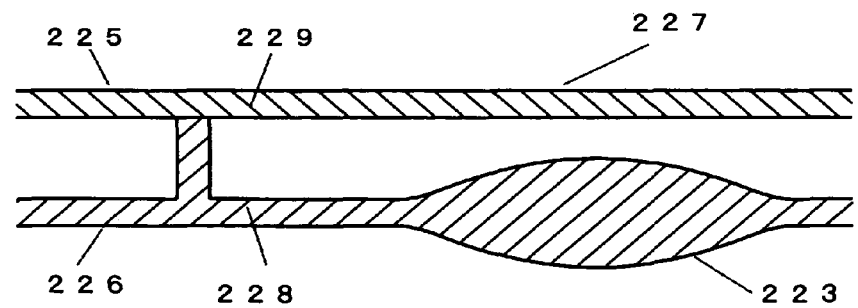

Air is then relieved of the reactor tank section 223 and the flow paths connected to the reactor tank section 223 as described above (Step 23) to fill the reactor tank section 223 with the buffer liquid as well, as shown in FIG. 7B. The valves 212b and 212d are closed and the valves 212a and 212c are opened. This causes the sample liquid dropped into the port 202a for sample liquid introduction to suctioned and fed through a sample liquid supply path 225 and the waste liquid path 227 to the waste liquid tank 800. Air is then relieved of the sample liquid supply path 225 and the waste liquid path 227 (Step 24) to fill these components with the sample liquid, as shown in FIG. 7C. In this way, the air relief of each flow path is completed. At the time, the sample liquid supply path 225 and the waste liquid path 227 are, broadly speaking, filled with the sample liquid while the buffer liquid supply path 226, the branch flow path section 229, and the reactor tank section 223 are filled with the buffer liquid.

Figure 7D:
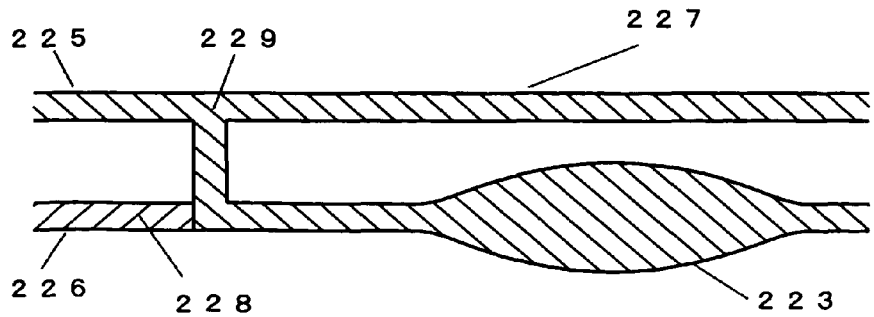

The valves 212a and 212c are then closed again and the valves 212b and 212d are opened to cause the buffer liquid in the buffer liquid supply path 226 to be suctioned and fed through reactor tank section 223 to the waste liquid tank 800, when the suction force of a trace liquid feed pump 901 is also adjusted to cause the buffer liquid to flow at a predetermined flow rate (Step 25). Upon completion of the adjustment of the trace liquid feed pump 901, the valve 212*b* is closed to stop feeding the buffer liquid. The valve 212*a* is then opened to feed the sample liquid through the sample liquid supply path 225 and the branch flow path section 229 to the reactor tank section 223, as shown in FIG. 7D.

Specifically, the sample liquid fed from the sample liquid supply path 225 carries away the buffer liquid that fills the branch flow path section 229 and the reactor tank section 223 and flows into the reactor tank section 223. At the time, the ligand with which the reactor tank section 223 is modified reacts with an analyte in the sample liquidm, thus causing bond reaction. The prevailing change in the resonant frequency of a crystal oscillator is then measured and the state of reaction is detected (Step 26). Because, at Step 25, the trace liquid feed pump 901 is under proper adjustment, the sample liquid is fed into the reactor tank section 223 at a predetermined flow rate and bond reaction is in progress on a predetermined condition.

Considering this flow rate, the valve 212*a* is closed at an appropriate timing and the suction operation of the trace liquid feed pump 901 is stopped and a predetermined amount of sample liquid is fed accurately to the reactor tank section 223. This results in the completion of the bond reaction. As an example of analysis requirements, the amount of the sample liquid used in the reaction is 50 µl and the reaction time is, for example, 5 to 50 minutes. The flow rate of the sample liquid by the operation of the trace liquid feed pump 901 is also 0.1 to 10 µl/min.

Concentration equilibrium is then reached and there is not much bond between the analyte and the ligand, thus stopping a change in the resonant frequency. The supply of a predetermine of the sample liquid is then completed and the buffer liquid is fed into the reactor tank section 223. The analyte and the ligand once bonded then undergoes partial dissociation, thus resulting in a small change in the resonant frequency. The detection of the state of the dissociation is effective for knowing the strength of the bond between the analyte and the ligand, for example.

As described above, using the micro reactor chip 2000 according to the second embodiment allows the detection of a substance contained in the sample liquid. However, the micro reactor chip, particularly the crystal substrate 100 and the reactor tank section 223 are not limited to the configurations described above. An example of a configuration for holding the crystal substrate 100 is, shown in FIG. 11.

Figure 11A:
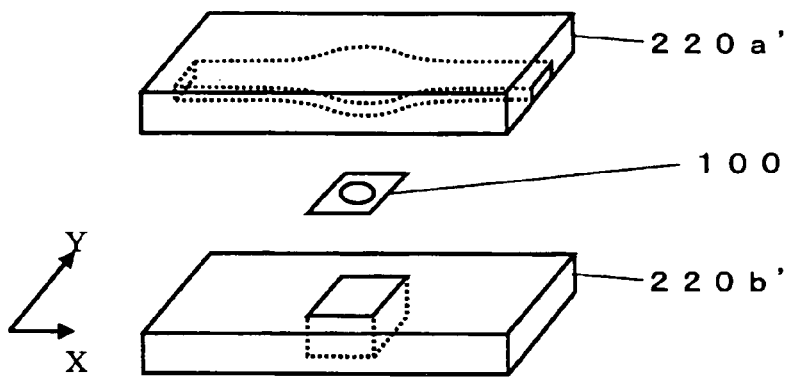
FIG. 11A-11E are a process diagram showing a configuration for holding a crystal substrate on a micro reactor chip according to another embodiment of the present invention.
Figure 11B:
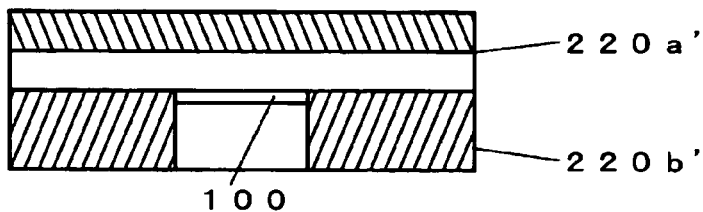
Figure 11C:
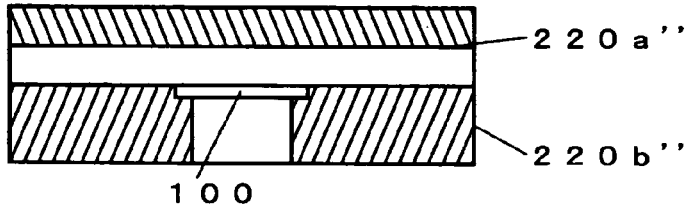

FIG. 11A shows a configuration in which a flow path substrates 220*a*' is formed with a groove that will act as a reactor tank section 223, a flow path substrate 220*b*' is formed with a through hole, and the crystal substrate 100 and the flow path substrates 220*a*' and 220*b*' are integratedly formed with the crystal substrate 100 between the flow path substrates. The cross section of the configuration is shown in FIG. 11B. The cross-direction (Y direction) end surface and the flow path substrates 220*a*' are bonded to the upper surface of the crystal substrate 100 while the longitudinal (X direction) side surface of the crystal substrate 100 is bonded to the flow path substrates 220*b*', thus holding the crystal substrate 100. Any clearance between bonding surfaces would cause sample liquid leaks or air bubbles in the sample liquid, which demands high-accuracy x-directional dimensions of the through hole in the flow path substrates 220*b*'. If a determined dimensional accuracy cannot be obtained, it is also possible to apply a mold agent to the interface (D) between the flow path substrates 220*b* and the crystal substrate 100 for clearance sealing. Alternatively, a stepped through hole is formed in the flow path substrates 220*b*'' and the crystal substrate 100 is fit into the stepped portion. This allows the area where the flow path substrates 220*b*'' are bonded to the crystal substrate 100 to be increased to improve air-tightness between the crystal substrate 100 and the external world. See FIG. 11C.

Figure 11D:
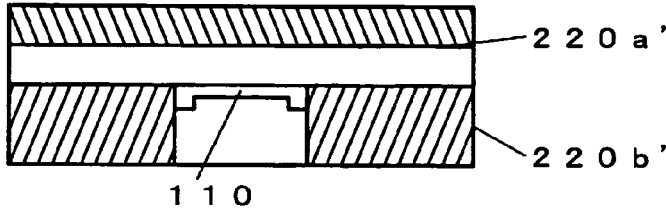
Figure 11E:
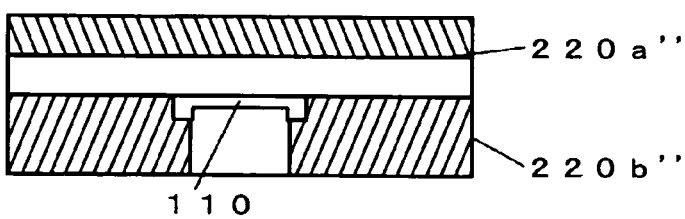

To increase detection sensitivity, it is also essential to increase the resonant frequency of the crystal oscillator. Increasing the resonant frequency requires a thinner crystal oscillator. However, a thinner crystal oscillator has a lower strength, thus raising a problem that the thinner crystal oscillator is difficult to mount. As a general method for solving the problem, a tray-like structure (mesa structure) having a thinner region including the electrode of the crystal oscillator is known. A crystal oscillator having such a mesa structure can realize a high resonant frequency while maintaining a high strength. An example of a configuration where a crystal substrate 110 having a mesa structure is shown in FIGS. 11D and 11E. The introduction of a crystal substrate 110 having such a mesa structure allows a higher detection sensitivity.

In the examples of the configuration shown in FIG. 11, a sample liquid is fed parallel to the surface of the crystal substrate 100, thereby producing a smooth flow the sample liquid. The sample liquid can therefore be fed to a adsorption film 609 at a stable flow rate and with a stable concentration, which allows high-accuracy detection.

Using the micro reactor chip 2000 and micro reactor system 2500 according to the second embodiment described above allows a flow path configuration to be very simple and compact and the chip and system to be manufactured in a simply manner. The absence of a mixture of the sample liquid the buffer liquid makes it possible to realize detection with high accuracy.

Third Embodiment

Figure 12:
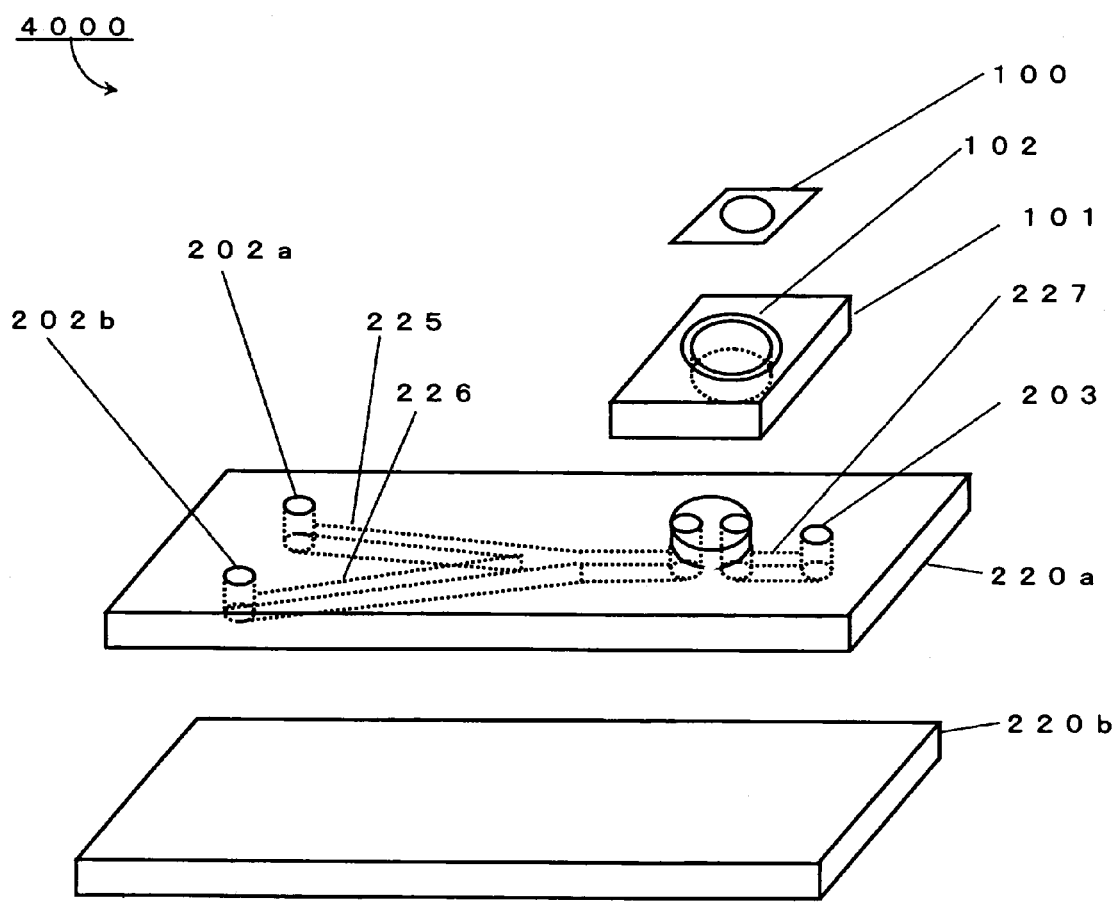
FIG. 12 is a perspective view showing a micro reactor chip according to another embodiment of the present invention.
Figure 13A:
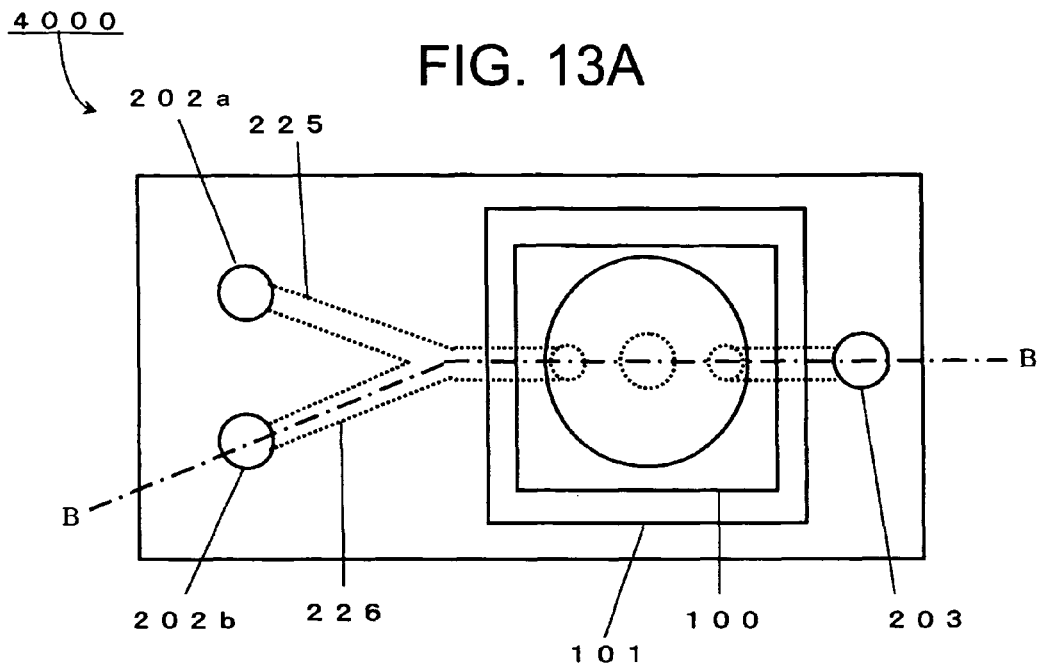
FIG. 13A-13B are a plan view of a micro reactor chip according to another embodiment of the present invention.
Figure 13B:
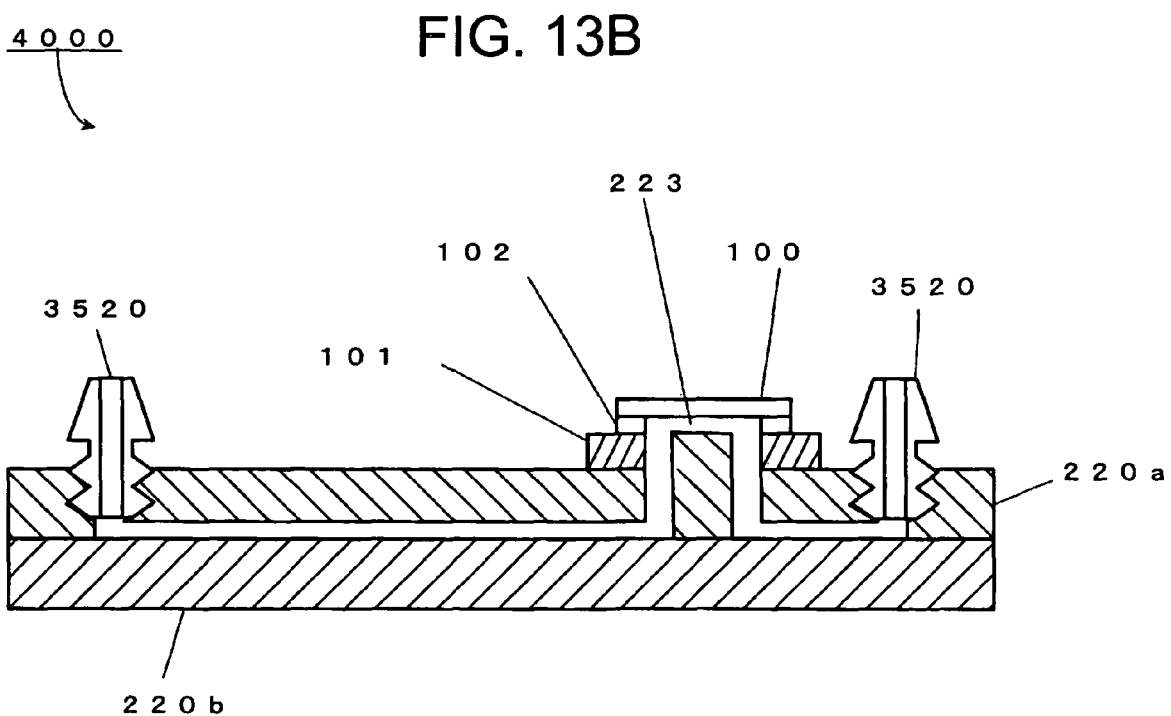

FIG. 12, FIG. 13A and FIG. 13B show an exploded perspective view of a micro reactor chip 4000 according to the invention, a schematic plan view of the micro reactor chip 4000 and a cross sectional view of the micro reactor chip 4000 taken along the surface B-B, respectively. The same descriptions as with the first and second embodiments described earlier will be not be made below.

The micro reactor chip 4000 includes a crystal substrate 100, a crystal holding substrate 101, and flow path substrates 220*a* and 220*b*, and a holding substrate 310, all of which are laminated together. Each of the members will be described below. The crystal substrate 100 is configured in the same way as in the first embodiment. The crystal substrate 100 is bonded through a ring film 102 to the crystal holding substrate 101 having a through hole. The flow path substrate 220*a* is provided with minute irregularities, a through hole and through holed threaded while the flow path substrate 220*b* is a flat plate.

The flow path substrate 220*a* and the flow path substrate 220*b* are laminated together. The crystal holding substrate 101 is also integrated with the flow path substrate 220*a* by fitting a convex portion in the flow path substrate 220*a* into the through hole in the crystal holding substrate 101, thereby providing a reactor tank section 223, where reaction occurs, a sample liquid supply path 225 for feeding a sample liquid for analysis, a buffer liquid supply path 226 for feeding a buffer liquid having a flow path cleaning function and a buffer function (dissociation function), and a waste liquid path 227 leading to a liquid discharge port 203.

A liquid introduction port 202*a*, which is the end of the sample liquid supply path (the end opposite to the waste liquid path), a liquid introduction port 202*b*, which is the end of the buffer liquid supply path (the end opposite to the reactor tank section 223), and a liquid discharge port 203 are provided with a connector 3520, which can be fixed using a screw.

Figure 14:
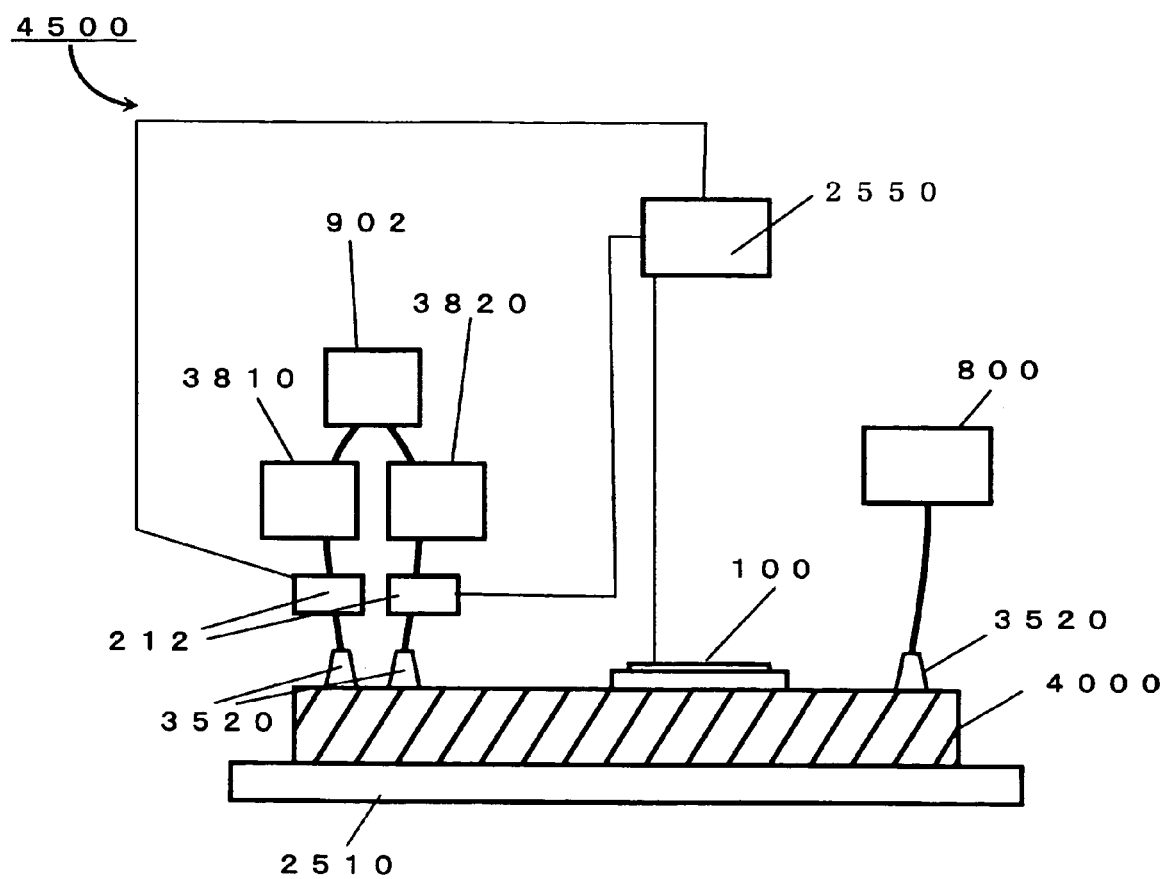
FIG. 14 is a cross sectional view showing a micro reactor chip according to another embodiment of the present invention.
Figure 15A:
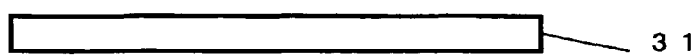
FIG. 15A-15F are a diagram showing a process for manufacturing a micro reactor chip according to another embodiment of the present invention.
Figure 15B:
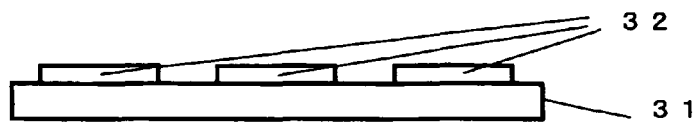
Figure 15C:
Figure 15D:
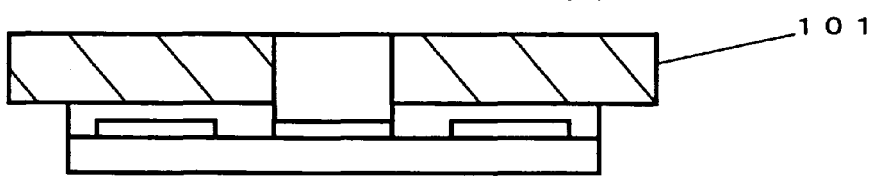
Figure 15E:
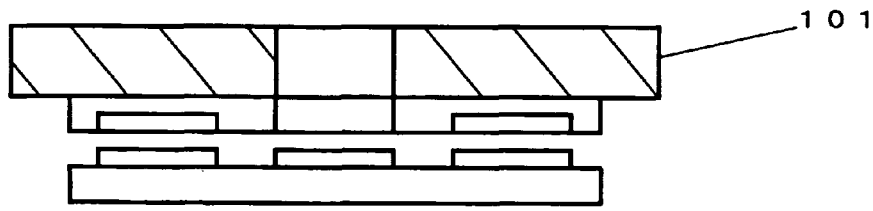
Figure 15F:
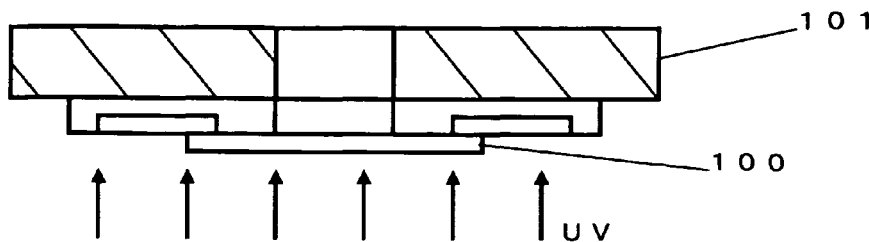

The configuration of a micro reactor system 4500 using the micro reactor chip 4000 will be then below with reference to a configuration view in FIG. 14. As with the second embodiment, the micro reactor chip 4000 is first provided on a stage 2510. A lead wire from each of a detection electrode 601 and an opposite electrode 602 on the crystal substrate 100 is used to obtain electrical conduction with the system.

A tube is connected to each of three connectors 3520 of the micro reactor chip 4000. Each connector can be easily connected to and disconnected from the tube because the elastic deformation of the tube itself is utilized for the connection between the connector 3520 and the tube.

Each of two tubes connected to the liquid introduction port 202a and 202b is connected to a sample liquid tank 3810 and a buffer liquid tank 3820 through a valve 212 that squeezes the tube to open and closes. A waste liquid tank 800 is also connected to the tube 3520 connected to the liquid discharge port 203. A pump 902 is also connected to each of the sample liquid tank 3810 and the buffer liquid tank 3820. When the pump 902 operates, a liquid stored in the sample liquid tank 3810 or the buffer liquid tank 3820 can be fed to the micro reactor chip.

In addition, a control circuit 2550 is connected to each of the pump 902, valve 212, and crystal substrate 100.

Liquid feeding for the micro reactor system 4500 will be described below. The pump 902 is first operated to apply a pressure to the inside of the sample liquid tank 3810 and the buffer liquid tank 3820. A sample liquid and a buffer liquid stored in the tanks try to flow through the tube and to a flow path in a micro reactor chip. However, a flow is produced in the micro reactor chip only with the valve 212 open. When the valve 212 provided on the buffer liquid supply path 226 is then opened, the buffer liquid flows from the buffer liquid tank 3820 through the tube, connector 3520, and buffer liquid supply path 226 into the reactor tank section 223. When the reactor tank section 223 is filled with the buffer liquid, the valve 212 connected to the buffer liquid supply path 226 is closed and the valve 212 on the sample liquid supply path 225 is opened. The sample liquid then flows from the sample liquid tank 3810 through the sample liquid supply path 225 into the reactor tank section 223. Liquids fed to these reactor tank sections 223 flow through the waste liquid path 227 and are accumulated in the waste liquid tank 800. The control circuit is responsible for all of the liquid feed described above and detection by sensor operation at a predetermined timing. The operation of the sensor for detection is performed as described for the second embodiment.

The configuration as described above allows the micro reactor system 4500 to be easily connected to and disconnect from the micro reactor chip 4000. The configuration described above is an example of the configuration of the system. The connection between the chip and the system is not limited to the above configuration.

A method for manufacturing a micro reactor chip 4000 will be then described below. As with the first and second embodiments, a crystal substrate 100 has an electrode formed on a polished AT-cut crystal plate 100. The crystal holding substrate 101 uses a glass plate and has a through hole, which has been provided by means of cutting. The flow path substrate uses a polycarbonate resin plate and has minute irregularities, a through hole, and a threaded hole, which have been formed by means of injection molding.

A process for bonding a crystal substrate 100 and a crystal holding substrate 101 to each other is shown in FIG. 15. A resist 32 is formed on a silicon wafer 31 (FIG. 15A) in a predetermined shape (FIG. 15B). A liquid PDMS 34 is then poured onto the wafer, which is then irradiated with ultraviolet light and the liquid PDMS is allowed to temporarily cure (FIG. 15C). The crystal holding substrate 101 is then placed on the temporarily cured PDMS 34 and the crystal holding substrate 101 side is irradiated with ultraviolet light, thereby causing the crystal holding substrate 101 and the PDMS plate 34 to bond to each other (FIG. 15D). The PDMS 34 is then removed from the through hole in the crystal holding substrate 101 (FIG. 15E). The PDMS 34 is then removed from the silicon wafer 31 and the crystal substrate 100 and the PDMS plate 34 are irradiated with ultraviolet light, thereby causing the crystal holding substrate 101 to be integrated with the crystal substrate 100 (FIG. 15F). A convex portion in the flow path substrate 220a is then fit into the through hole in the crystal holding substrate 101, thus allowing the micro reactor chip 4000 to be fabricated.

In this process, a glass plate has been used for the crystal holding substrate 101. It is also possible to prepare the micro reactor chip 4000 even by using a resin plate with glass coated with the surface thereof. The crystal holding substrate 101 and the flow path substrate 220a can be fixed to each other not only by means of fitting but also by means of bluing with a sealing tape and pressure welding using an O-ring. It is also possible to coat the surface of the flow path substrate 220a with glass, form a ring-like PDMS and bond the PDMS to the crystal holding substrate 101, for example.

To prevent air bubbles from entering a flow path, which cause noise in detection, it is also possible to make the wall of the flow path hydrophilic. As an example of a method for doing this, the concave portion and through hole in the flow path substrate 220a and the bonding surface of the flow path substrate 220b are sputtered with a hydrophilic film such as parylene before the crystal holding substrate is integrated with the flow path substrates 220a and 220b. Alternatively, After the crystal holding substrate is integrated with the flow path substrates 220a and 220b, it will be possible to form a hydrophilic film on the wall of the flow path in the process of pouring a liquid glass coating agent into the flow pass and allow the coating agent to cure, for example.

Because the PDMS is gas-permeable, feeding a reagent at a negative pressure causes ambient air to enter the flow pass through the PDMS from outside the micro reactor chip, thus generating air bubbles in the flow path. Consequently, it is possible to prevent air bubble from entering the flow path by adding a process of coating the chip formed with a coating agent that has a high gas barrier property from the outside of the PDMS portion to form a gas barrier film.

The above-mentioned configuration of the micro reactor chip 4000 allows a micro reactor chip to be easily manufactured even on a thin crystal substrate having high-frequency properties. It is because there is no external force from bonding between the crystal substrate and the flow path substrate or no damage to the crystal substrate held in manufacturing the chip. The above-mentioned configuration also allows the crystal substrate 100 integrated with the crystal holding substrate 101 to be easily bonded to the flow path substrate after ligand modification. When the above configuration is used, a ligand with the amount predetermined can be fixed on the crystal substrate 100 and without unwanted ligand on the wall of the flow path, thus allowing high-accuracy interaction analysis.

Fourth Embodiment

Figure 10A:
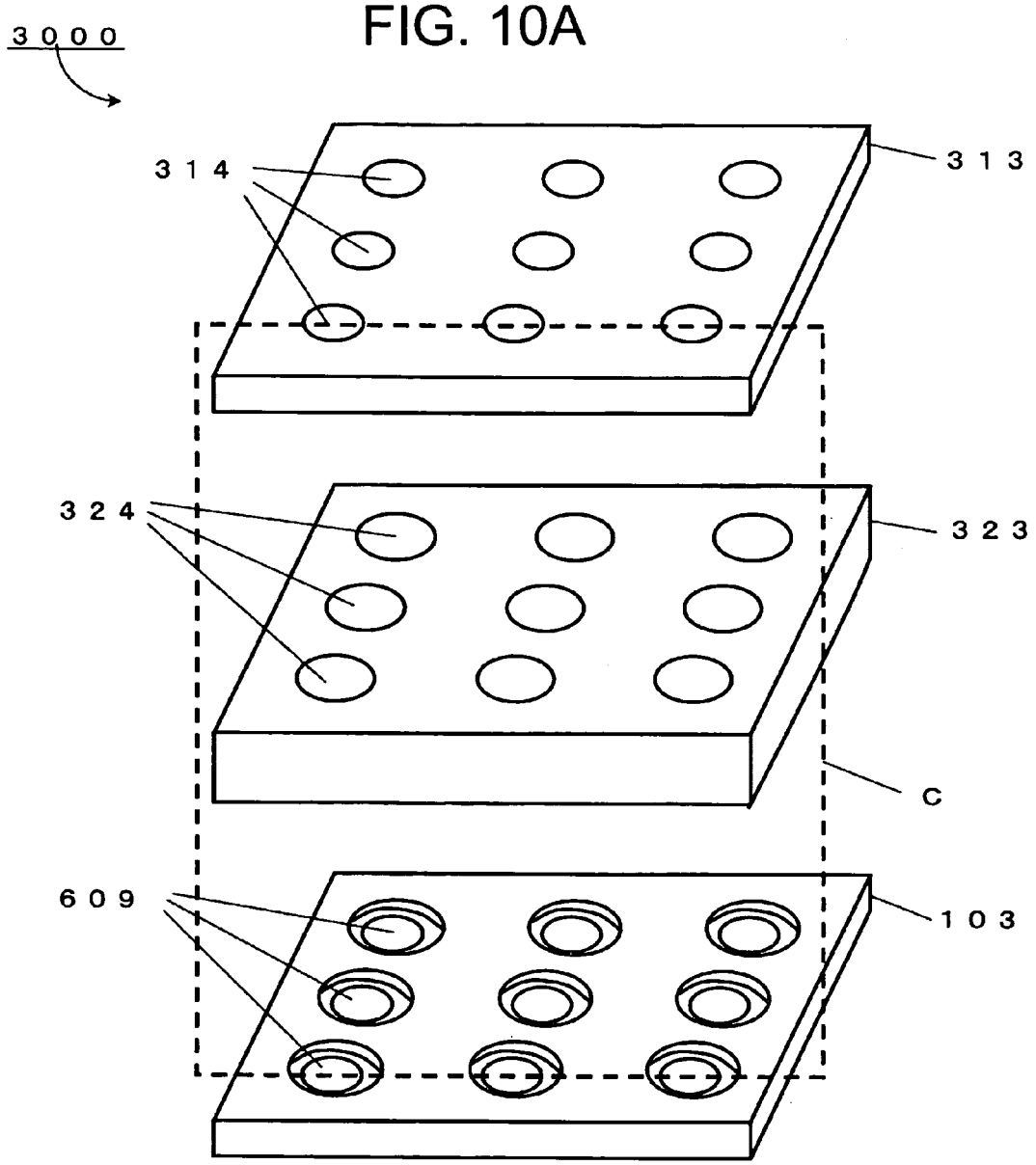
FIG. 10A-10B are a perspective view showing the configuration of a micro reactor chip according to another embodiment of the present invention.
Figure 10B:
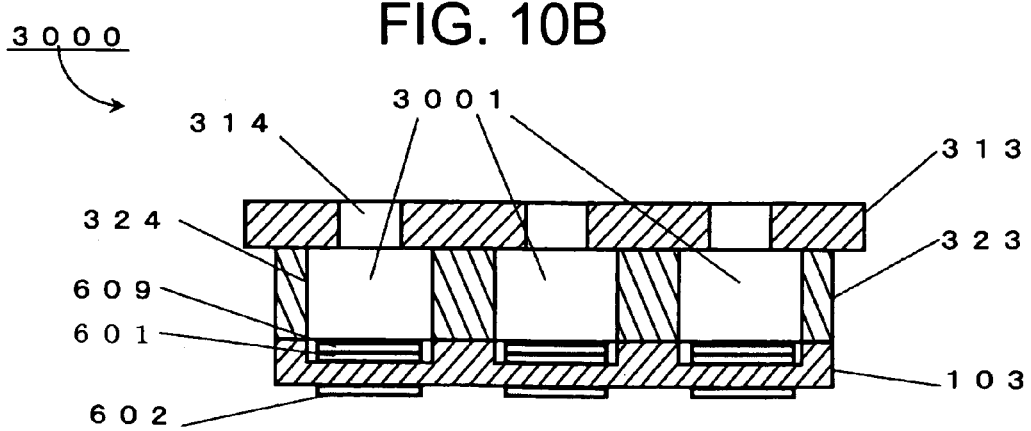

FIG. 10 shows a reactor 3000 according to the invention. Specifically, FIG. 10A shows an exploded perspective view of the reactor 3000 and FIG. 10B shown a cross sectional view of the reactor 3000 (the cross section taken along the surface C in FIG. 10A). The same descriptions as in the first embodiment described earlier will be not be made below.

The reactor 3000 includes a crystal substrate 103, a cell substrate 323, and a holding substrate 313, all of which are bonded to one another. The crystal substrate 1031 will first be described below. There are nine concave portions, each called a mesa structure, formed on one surface of the crystal substrate 103. A detection electrode 601 is provided inside each mesa structure. An opposite electrode 602 is provided on the opposite surface of each detection electrode 601. In addition, an adsorption film 609 for adsorbing only a specific substance is provided on the surface of the detection electrode 601. The cell substrate 323 is provided with nine through holes 324. Similarly, the holding substrate 313 is also provided with nine through holes 314.

These crystal substrate 103, cell substrate 323, and holding substrate 313 are integrated with one another, thus forming a reactor 3000. Specifically, the mesa structures of the crystal substrate 103 provided with the detection electrode 601 serve as a bottom and through holes 314 serve as openings and nine cells 3001, substantially circular concave portions, are formed.

When a sample liquid to be analyzed is dropped onto one of these cells 3001, the sample liquid is stored inside the cell 3001 and the adsorption film 609 provided above the detection electrode 601 becomes soaked with the sample liquid. At the time, an AC voltage is applied between the detection electrode 601 and the opposite electrode 602, both of which are opposite to each other on the crystal substrate. The change in the resonant frequency is then measured. This allows the measurement of the mass of a substance fixed by the adsorption film 609.

One cell has been described above. However, it is also possible to drop a sample of a different type onto each of a plurality of cells 301 provided on the reactor 300 and perform detection at the same time. It is also possible to provide each cell 3001 with each of adsorption films 609 of different types and drop one type of sample onto a plurality of cells 301 at one time for simultaneous detection. Note that the through hole 314 is smaller than the through 324 and the cell 3001 has a concave portion with a narrow opening. This is done to prevent a change in the concentration of the sample liquid due to evaporation during measurements. Any change in the concentration may hinder accurate detection.

The chemical reaction of a specific substance occurs only on the surface of the adsorption film 609. It is therefore desirable that a mechanism for agitating the sample liquid in the cell 3001 (the agitating operation of the entire sensor due to vertical or horizontal oscillations, for example) should be available.

A method for manufacturing the reactor 3000 will be then described below. A mesa structure is first formed on one surface of an AT-cut crystal wafer 103 utilizing photolithography. Both surfaces of the mesa structure are deposited or sputtered with gold to prepare wiring to the detection electrode 601, opposite electrode 602, and each electrode. A through hole 324 is then formed in a polydimethylsiloxane (PDMS) plate to fabricate a cell substrate 323. A through hole 314 is then formed on a silicon wafer to fabricate a holding substrate 313. When these substrates are laminated together and pressed, a siloxane bond occurs at the interface among the substrates, thus allowing the three substrates to be bonded to one another.

As described above, providing a plurality of cells on a sensor allows the simultaneous detection of a plurality types of substances. The configurations and manufacturing method described above are simple and cause no residual stresses on the crystal oscillator or unwanted oscillation modes, thus allowing high detection sensitivity to be maintained.

What is claimed is:

1. A reactor comprising:
    a main body having a flow path substrate made of silicone and a crystal substrate having a surface bonded to a surface of the flow path substrate, the surface of the flow path substrate having a concave portion forming with the surface of the crystal substrate a flow path for running a sample to be measured and a reactor tank connected to the flow path;
    capture means disposed in the reactor tank for capturing a specific substance contained in the sample to be measured; and
    a sensor configured to measure a physical quantity of the specific substance contained in the sample and captured by the capture means, the sensor including a crystal oscillator comprising at least a portion of the surface of the crystal substrate and configured to be excited by a plurality of electrodes above which the reactor tank is disposed, and including frequency measuring means connected to the plurality of electrodes for measuring a change in frequency of the crystal oscillator;
    wherein the plurality of electrodes comprise a first electrode disposed on a first surface of the crystal substrate and a second electrode disposed on a second surface of the crystal substrate opposite to the first surface, the first electrode comprising a detection electrode on which the reactor tank is directly disposed.

2. A reactor according to claim 1; wherein the sensor is configured to measure a mass of the specific substance contained in the sample.

3. A reactor according to claim 1; wherein the crystal substrate has a mesa structure in which a region of the plurality of electrodes forms a bottom of the reactor tank.

4. A reactor according to claim 1; wherein the frequency measuring means comprises a variable-frequency AC power supply and an ammeter, both connected in series to the plurality of electrodes of the crystal oscillator.

5. A reactor according to claim 1; wherein the frequency measuring means comprises a frequency meter that measures an oscillation frequency of an oscillation circuit incorporating therein the crystal oscillator.

6. A reactor according to claim 1; wherein the flow path has one or more through-holes passing through the flow path substrate for introducing into the reactor tank and discharging from the reactor tank the sample to be measured.

7. A micro-reactor chip comprising:
    a flow path substrate made of silicone and having a flow path for running a sample to be measured, an introduction port for introducing the sample to be measured into a reactor tank through the flow path, and a discharge port for discharging the sample to be measured from the reactor tank through the flow path;
    a crystal substrate having a surface bonded to a surface of the flow path substrate, the surface of the flow path substrate having a concave portion that forms with the surface of the crystal substrate the reactor tank;
    capture means disposed in the reactor tank for capturing a specific substance contained in the sample to be measured; and
    a sensor that measures a physical quantity of the specific substance contained in the sample and captured by the capture means, the sensor comprising at least a portion of the crystal substrate and including a plurality of electrodes above which the reactor tank is disposed, the plurality of electrodes comprising a first electrode disposed on a first surface of the crystal substrate and a second electrode disposed on a second surface of the crystal substrate opposite to the first surface, the first electrode comprising a detection electrode on which the reactor tank is directly disposed.

8. A micro-reactor chip according to claim 7; wherein the flow path substrate has a valve mechanism disposed in the flow path for closing and opening the flow path.

9. A micro-reactor chip according to claim 7; wherein the flow path substrate comprises a plurality of laminated substrate members formed with at least any of a concave portion, a groove and a through-hole.

10. A micro-reactor chip according to claim 7; wherein the crystal substrate has a mesa structure with a predetermined region that includes the plurality of electrodes.

11. A micro-reactor chip according to claim 7; wherein the flow path substrate has a stepped portion in a predetermined region thereof bonded to the crystal substrate for supporting the crystal substrate.

12. A micro-reactor system comprising:
a micro-reactor chip according to claim 10;
frequency measuring means connected to the plurality of electrodes of the sensor for measuring a change in frequency;
pump means connected to the introduction port or the discharge port of the flow path substrate for feeding the sample to be measured;
feed control means for controlling the opening and closing of a valve mechanism operable to open and close the flow path of the flow path substrate; and
control means for controlling the pump means, the frequency measuring means, and the feed control means.

13. A reactor according to claim 1; wherein the first surface of the crystal substrate is disposed in the reaction tank; and wherein the capture means comprises an adsorption film disposed on first surface of the crystal substrate.

14. A reactor comprising:
a base substrate made of silicone and having a groove, an introduction port that opens into the groove for introducing a sample to be measured, and a discharge port that opens into the groove for discharging the sample to be measured;
a crystal substrate having a surface bonded to a surface of the base substrate, the crystal substrate overlying the groove of the base substrate to form a flow path defined by the surface of the crystal substrate and the groove of the base substrate, a region of the groove of the base substrate in the chemically bonded state of the crystal substrate and the base substrate forming a reactor tank that is disposed in the flow path so that a sample to be measured that is introduced into the introduction port passes through the reactor tank and is discharged through the discharge port;
an adsorption film for adsorbing a specific substance contained in the sample to be measured; and
a measuring device that measures a physical quantity of the specific substance adsorbed by the adsorption film, the measuring device including a detection electrode above which the reactor tank is disposed, the detection electrode being disposed on the surface of the crystal substrate, and the adsorption film being disposed directly over and in contact with the detection electrode;
wherein the measuring device includes another electrode disposed on a surface of the crystal substrate opposite to the surface of the crystal substrate on which the detection electrode is disposed.

15. A reactor according to claim 14; wherein the measuring device comprises a frequency measuring device connected to the detection electrode for measuring a change in frequency.

* * * * *

UNITED STATES PATENT AND TRADEMARK OFFICE
CERTIFICATE OF CORRECTION

| | |
|---|---|
| PATENT NO. | : 8,828,321 B2 |
| APPLICATION NO. | : 11/338293 |
| DATED | : September 9, 2014 |
| INVENTOR(S) | : Yoko Shinohara et al. |

It is certified that error appears in the above-identified patent and that said Letters Patent is hereby corrected as shown below:

IN THE CLAIMS

Claim 1, Column 16:

Line 8, change "surface" to --generally flat shape with opposed first and second major surfaces and being--;

Line 10, delete "the";

Line 11, delete "surface of";

Line 20, delete "of the surface";

Line 27, change "a first" to --the first major--;

Line 28, change "a second surface" to --the second major surface--; and

Line 29, change "first surface" to --first major surface--.

Claim 7, Column 16:

Line 57, change "having a surface" to --having a generally flat shape with opposed first and second major surfaces and being--;

Line 59, delete "the"; and

Line 60, delete "surface of".

Signed and Sealed this
Eighth Day of March, 2016

Michelle K. Lee
*Director of the United States Patent and Trademark Office*

CERTIFICATE OF CORRECTION (continued)
U.S. Pat. No. 8,828,321 B2

IN THE CLAIMS

Claim 7, Column 17:

Line 3, change "a first surface" to --the first major surface--;

Line 4, change "a second surface" to --the second major surface--; and

Line 5, change "first surface" to --first major surface--.

Claim 14, Column 18:

Line 9, change "having a surface" to --having a generally flat shape with opposed first and second major surfaces and being--;

Line 12, delete "the surface of";

Line 14, delete "chemically";

Line 26, change "the surface" to --the first major surface--;

Line 30, change "a surface" to --the second major surface--; and

Line 31, change "the surface" to --the first major surface--.